United States Patent [19]

Ando et al.

[11] 4,161,424
[45] Jul. 17, 1979

[54] NOVEL ENDONUCLEASE AND PROCESS FOR PRODUCTION THEREOF

[75] Inventors: Tadahiko Ando, Tokyo; Takehiko Shibata; Shukuko Ikawa, both of Wako; Cholung Kim, Tokyo, all of Japan

[73] Assignee: Rikagaku Kenkyusho, Wako, Japan

[21] Appl. No.: 816,541

[22] Filed: Jul. 18, 1977

[30] Foreign Application Priority Data
Jul. 23, 1976 [JP] Japan .................................. 51-87883

[51] Int. Cl.² ...................... C07G 7/026; C12D 13/06
[52] U.S. Cl. .................................................. 435/199
[58] Field of Search ............... 195/62, 65, 66 R, 28 N

[56] References Cited

U.S. PATENT DOCUMENTS

| | | | |
|---|---|---|---|
| 3,956,064 | 5/1976 | Horikoshi et al. | 195/28 N |
| 4,064,011 | 12/1977 | Mayer et al. | 195/65 |
| 4,080,261 | 3/1978 | Shibata et al. | 195/62 |

*Primary Examiner*—Lionel M. Shapiro
*Attorney, Agent, or Firm*—Bucknam and Archer

[57] ABSTRACT

The present invention relates to novel enzymes which decompose nucleic acid and are endowed with a substrate specificity recognizing specific biological deoxyribonucleic acid and cleaving specific bonds thereof to produce fragments of deoxyribonucleic acid of specific sizes and which are obtained by culturing microorganisms belonging to genus Bacillus and purifying the cell free extract thereof by such treatment as streptomycin treatment, ammonium sulfate precipitation, ion exchange chromatography, gel filtration or combination of these processes.

23 Claims, 3 Drawing Figures

FIG. I-I
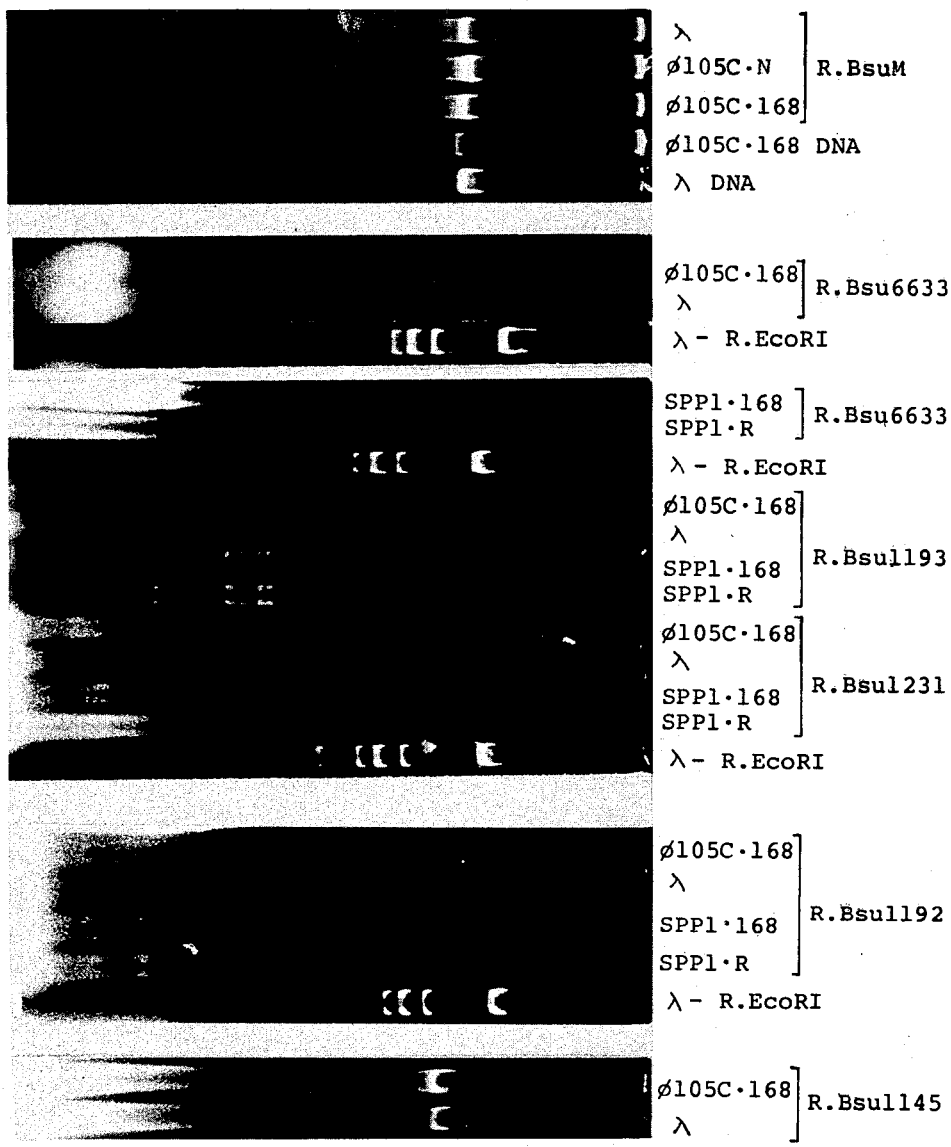

NOVEL ENDONUCLEASE AND PROCESS FOR PRODUCTION THEREOF

FIELD OF THE INVENTION

The present invention relates to novel enzymes which decompose nucleic acid and are endowed with a substrate specificity recognizing specific biological deoxyribonucleic acid and cleaving specific bonds thereof to produce fragments of deoxyribonucleic acid of specific sizes and to a process for production thereof.

Enzymes (DNase) which decompose doexyribonucleic acid (DNA) exist in various biological materials, participate in the important processes of the life phenomena such as metabolism, decomposition, synthesis, substitution of DNA, and have recently drawn particular attention because of their enzymatic chemical characteristics and biological functions. On the other hand, in the study of the structure and function of DNA of the gene, these enzymes have become a powerful means in the production and separation of enzymes having specific action, in the application and development as a biochemical reagent, and in the molecular cloning of the gene.

DNA decomposing enzymes are roughly classified into exonuclease and endonuclease according to their function. The former type acts from the terminal of the polynucleotide chain of the molecule of DNA and successively liberates and decomposes nucleotide, and the latter type forms fragments of DNA or oligonuclotide by cleaving phosphodiester bond in the DNA molecule.

DESCRIPTION OF THE PRIOR ART

Recently, in the study of endonuclease type enzymes, great progress has been achieved in the studies on enzymes which show a specificity to the structure of DNA, particularly to the configuration of nucleotide or to the structural change which exists in nature or is introduced artificially, on enzymes which act by recognizing a specific biological DNA, and on enzymes which have biologically important function (refer to Tadahiko Ando, Chemistry and Life, Vol. 13, No. 6, p. 342 (1975)).

The present inventors performed the following studies and established methods for production of each enzyme. By a series of studies the present inventors accomplished methods for producing enzymes, more particularly a method for producing enzymes from the culture of Aspergilus oryzae, which do not act upon double-stranded DNA and specifically decompose single-stranded DNA (Japanese Pat. No. 593,368); a method of producing enzymes from the fungus of Aspergilus oryzae which preferentially decompose purine-purin bond (Japanese Pat. No. 621,205); a method of producing enzymes which introduce a limited number of single-strand breaks in duplex DNA obtained from Escherichia coli infected with bacteriophage (Japanese Pat. No. 764,919); a method of producing an enzyme which hydrolyzes RNA to nucleooside-2,3-cyclic phosphate obtained from Escherichia coli infected or induced by bacteriophage (Japanese Patent Application No. 78869/1972, Japanese Patent Disclosure No. 35577/1974); a method of producing enzymes which preferentially cleave guanine-guanine bond in the molecule of DNA, from the culture liquid of alkalophilic bacteria microbes (Japanese Patent Application No. 114131/1973, Japanese Patent Disclosure No. 64484/1975); a method of producing enzyme which specifically decompose RNA moiety of DNA-RNA hybrid obtained from the cells of Bacillus subtilis (Japanese Patent Application No. 127276/1974); and a method of producing enzymes having a substrate specificity recognizing specific biological deoxyribonucleic acid and cleaving specific bonds thereof, from Bacillus subtilis and genus Bacillus (Japanese Patent Application No. 121671/1975, Japanese Patent Disclosure No. 47980/1977).

SUMMARY OF THE INVENTION

Heretofore, studies have centered on the phenomena that the host-range of phage is controlled by host and on host controlled modification and restriction and it has been found that there is a mechanism whereby Escherichia coli modifies λ phage DNA and controls unmodified foreign DNA.

While eagerly studying novel enzymes which decompose DNA produced by various microorganisms, the inventors have succeeded in collecting new enzymes which decompose DNA and are endowed with a specificity to segment at specific positions in the molecule of DNA by recognizing DNA of a specific biomicrobe obtained from the cells of aerobic bacillus with spore belonging to genus Bacillus of 62 strains, and to form fragment of DNA of specific size, and have completed this invention.

Therefore, the object of the present invention is to provide enzymes having the specific biological activity above mentioned.

Another object of the present invention is to provide a process for producing said enzymes.

BRIEF DESCRIPTION OF THE DRAWING

The drawing is a photograph showing the results of agarose gel electrophoresis of phage DNA treated by the present enzymes.

The symbols in the drawing have the following meanings.

Figures 1, 2:
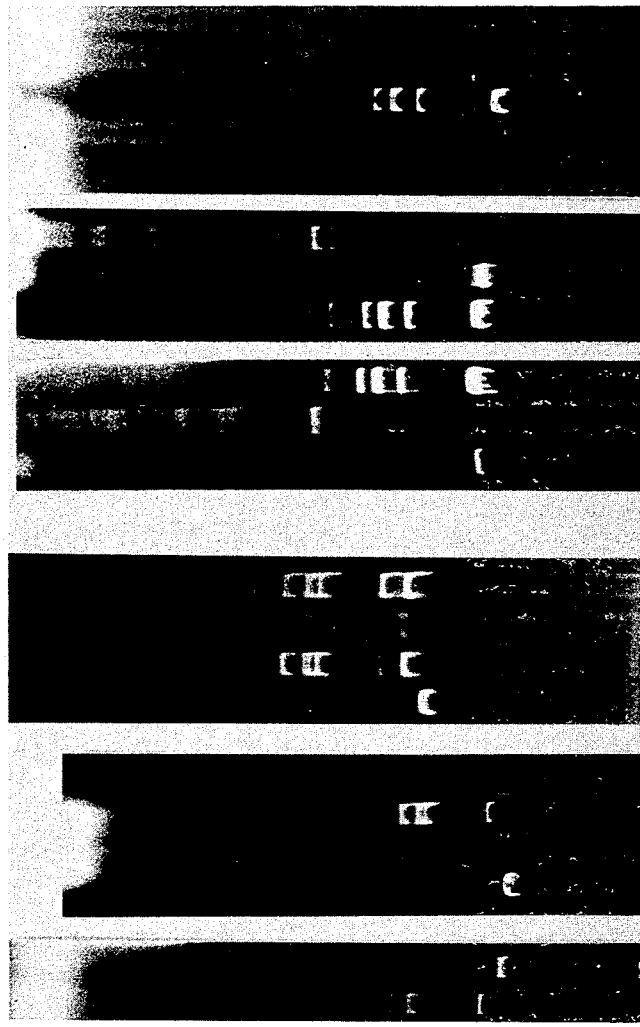
Figures 1, 2, 3:
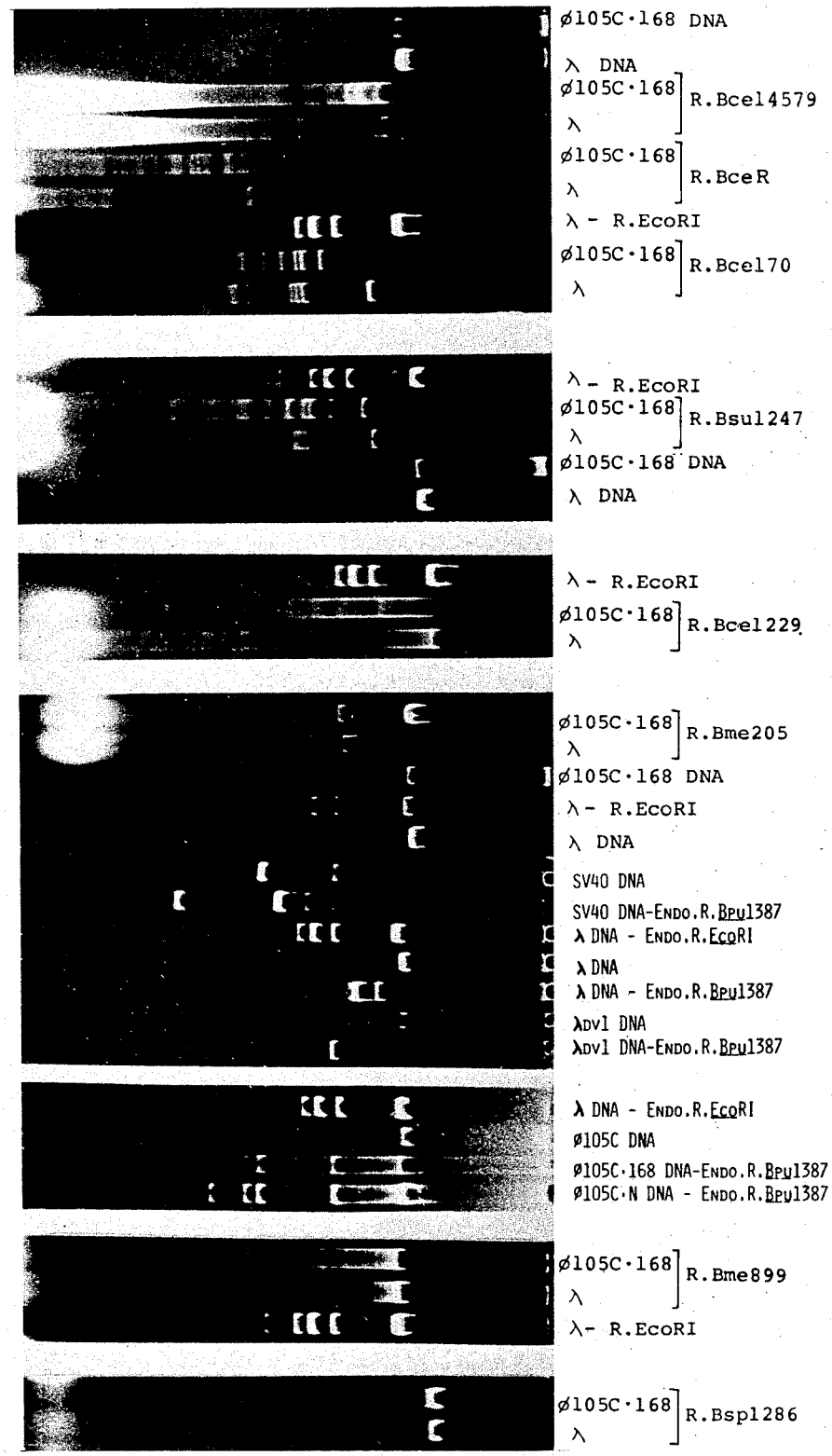

φ105C.168—Bacillus phage φ105C grown on Bacillus subtilis ATCC 6051

SPP1.168—Bacillus phage SPP1 grown on Bacillus subtilis ATCC 6051

φ104C.N—Bacillus phage φ105C grown on Bacillus amyloliquefaciens IAM1522

SPP1.R—Bacillus phage SPP1 grown on Bacillus subtilis R

λ—DNA of E.coli phage λ grown on Escherichia coli B

λH—DNA modified by Bacillus amyloliquefaciens H

λDNA—untreated λDNA grown on Escherichia coli B

φ105C.168DNA—untreated φ105C.168DNA

R.EcoRI—DNA of E.coli phage λ treated with EcoRI enzyme of Escherichia coli

DESCRIPTION OF THE PREFERRED EMBODIMENTS

It is a characteristic of the present enzymes that they are capable of recognizing specific nucleic acids and selectively cleaving the phosphodiester bond in the nucleic acids to produce nucleic acid fragments having discrete molecular weight, and the enzymes are obtained from a cell free extract of the species belonging to genus Bacillus.

The microorganisms used to obtain the present enzymes belong to Genus Bacillus, and any of the strains belonging to genus Bacillus and having an ability to produce the present enzyme can be used in this invention; for example *Bacillus subtilis* which was deposited in an unrestricted form with the Institute of Applied Microbiology, University of Tokyo (Address: 1-1, Yayoi, Bunkyoku, Tokyo, Japan) as IAM 1076, 1114, 1145, 1192, 1193, 1231, 1247, 1259 and 1523; *Bacillus cereus* which was deposited in unrestricted form as IAM 1229; *Bacillus megaterium* which was deposited in unrestricted form as IAM 1030; *Bacillus sphaericus* which was deposited within an unrestricted form as IAM 1286, and *Bacillus pumillus* which was deposited in unrestricted form with the Faculty of Agriculture, Hokkaido University (Address: Nishi-9-chome, Kita-9-jo, Sapporo City, Hokkaido, Japan) as AHU 1387 (see JFCC Catalogue of Culture (1966)), these microorganisms being freely available to any third party at any time.

On the other hand, the species of *Bacillus subtilis* were assigned the American Type Culture Collection (12301 Parklawn Drive Rockville, Md. 20852) ATCC access numbers 6051 and 6633; the species of *Bacillus amyloliquefaciens* the ATCC access number 23350; the species of *Bacillus cereus* the ATCC access number 14579; the species of *Bacillus cereus* Rf sm st the ATCC 31293; the species of Bacillus sp. No. 170 the ATCC access number 31292, and the species of *Bacillus megaterium* B 205-3 the ATCC access number 31294, all of which are on deposit with ATCC in an unrestricted deposit permitting the public full access to the cultures. The species of ATCC 6051, 6633, 23350 and 14579 were released for distribution to the public on June 9, 1977 (See ATCC Catalogue of Strains (1974)).

The species of ATCC 31292, 31293 and 31294 were released for distribution to the public on June 10, 1977.

The applicant will maintain the deposition of IAM 1076, 1114, 1145, 1192, 1193, 1231, 1247, 1259, 1523, 1229, 1030 and 1286, and AHU 1387, and ATCC 6051, 6631, 23350, 14579, 31292, 31293 and 31294 in the unrestricted form until the end of the duration of a patent granted on this application if a patent is granted on the present application, and thus the said microorganism strains will be available to any third party at any time until the end of the duration of the patent granted on the present application.

Table 1

| Microorganism | Depository | Deposition No. |
|---|---|---|
| Bacillus subtilis | The American Type Culture Collection (ATCC) | ATCC 6051 |
| " | " | ATCC 6633 |
| " | The Institute of Applied Microbiology, University of Tokyo(IAM) | IAM 1076 |
| " | " | IAM 1114 |
| " | " | IAM 1145 |
| " | " | IAM 1192 |
| " | " | IAM 1193 |
| " | " | IAM 1231 |
| " | " | IAM 1247 |
| " | " | IAM 1259 |
| Bacillus amyloliquefaciens | ATCC | ATCC 23350 |
| " | IAM | IAM 1523 |
| "Bacillus subtilis" | | |
| Bacillus cereus | ATCC | ATCC 14579 |
| Bacillus cereus Rf sm st | ATCC | ATCC 31293 |
| Bacillus cereus | IAM | IAM 1229 |
| Bacillus sp. No. 170 | ATCC | ATCC 31292 |
| Bacillus megaterium | IAM | IAM 1030 |
| Bacillus megaterium B 205-3 | ATCC | ATCC 31294 |

Table 1-continued

| Microorganism | Depository | Deposition No. |
|---|---|---|
| Bacillus pumillus | Faculty of Agriculture, Hokkaido University (AHU) | AHU 1387 |
| Bacillus sphaericus | IAM | IAM 1286 |

Microbiological properties of the strains deposited at the American Type Culture Collection, namely Bacillus sp. No. 170 (ATCC 31292), *Bacillus cereus* Rf sm st (ATCC 31293) and *Bacillus megaterium* B 205-3 (ATCC 31294) will now be described.

The tests described below were conducted according to the methods described in R. E. Gordon, W. C. Haymes & C. H-N. Pang, "The Genus Bacillus," U.S. Dept. Agr., 1973 and "Bergey's Manual of Determinative Bacteriology," 1974.

(1) Microbiological Properties of Bacillus sp. No. 170

(A) Morphology

The strain has a monococcal or streptococcal rod-like shape having a size of $(1.0-1.2) \times (3.0 \times 5.0)$ m$\mu$ and it has peritrichous flagella and a moving property. It is positive to the Gram staining test and negative to the acid fast test. The strain has no pleomorphism and forms oval spores. The composition of the medium used for the morphological observation is as follows:
Peptone: 10 g/l
Meat extract: 10 g/l
NaCl: 5 g/l
Agar: 15 g/l
pH: 7.2

(B) Growth on Various Media (1) Bouillon-Agar Plate Culture: The colony is circular and forms a flat ridge, and the peripheral edge is wavy. The surface of the colony is smooth and white. No pigment is formed in the culture medium.

(2) Bouillon-Agar Streak Culture: The growth is medium and spread. The surface is smooth and white. No pigment is formed in the culture medium.

(3) Bouillon Liquid Medium: The surface of the culture medium is membranous and sedimented precipitates are formed.

(4) Bouillon-Gelatin Stab Culture: Gelatin is liquefied.

(5) Litmus Milk: The litmus color disappears and peptonization takes place.

(C) Biological Properties:

(1) Nitrate Reduction: positive
(2) Denitrification: negative
(3) MR Test: positive
(4) VP Test: positive
(5) Formation of Indole: negative
(6) Formation of Hydrogen Sulfide: negative
(7) Hydrolysis of Starch: positive
(8) Utilization of Citric Acid: The strain grows on Christensen medium but it does not grow on Koser medium.
(9) Utilization of Inorganic Nitrogen: The strain can grow by utilizing an ammonium salt.
(10) Production of Pigment: negative
(11) Urease: negative
(12) Oxidase: positive

(13) Catalase: positive

(14) Growth Conditions:
Optimum pH: 7 to 10
Optimum Temperature: 30° to 37° C.

(15) Behavior to Oxygen: aerobic

(16) O-F Test: The strain forms an acid either aerobically or anaerobically.

(17) Utilization of Carbon Sources:
The strain forms acids either aerobically or anaerobically from D-glucose, D-mannose, D-fructose, maltose, sucrose, trehalose, glycerol and starch. Generation of a gas is not observed in any saccharide.

Formation of an acid or generation of a gas is not observed in case of L-arabinose, D-xyrose, D-galactose, lactose, Raffinose, D-sorbitol, D-mannitol and inositol.

(18) Salt Resistance: The strain can grow at an NaCl concentration of up to 7.5%.

(19) Hydrolysis of Casein: positive

(20) Phenylalanine Deaminase: negative

Reference to the above-mentioned literature in the light of the foregoing microbiological properties indicates that Bacillus sp. No. 170 (hereinafter referred to as "strain No. 170") belongs to the genus Bacillus. Comparison of strain No. 170 with strains belonging to the genus Bacillus reveals that it resembles *Bacillus cereus* but differs from *Bacillus cereus* in the point that strain No. 170 grows well under an alkaline condition through the growth pH of the known strain is in the range of from 5 to 8.

As pointed out hereinafter, strain No. 170 exhibits a maximum penicillinase production in an aklaline culture medium and it clearly differs from *Bacillus cereus* that produces a penicillinase in a neutral culture medium.

Accordingly, it was found that strain No. 170 is not in agreement with any known strain and it was judged reasonable to determine that strain No. 170 is a novel strain belonging to the genus Bacillus.

(2) Microbiological Properties of *Bacillus cereus* Rf sm st (A) Morphology

The strain is an aerobic bacillus forming endospores and is negative to the Gram staining test. The spore has an oval or cylindrical shape. The GC content in DNA is 32 to 37%.

(B) Biological Properties (1) Egg Yolk Test: positive (2) Growth Conditions: The highest temperature for strain growth is 35° to 45° C. and the lowest temperature is 0° to 20° C.

(3) Nitrate Reduction: positive (C) Growth on Media

The strain grows in an agar medium under an anaerobic condition. It grows in a medium containing 0.001% of lysozyme.

Reference to the above-mentioned literature indicates that the strain is substantially in agreement with known *Bacillus cereus*, and the strain was identified to be a strain of *Bacillus cereus*.

(3) Microbiological Properties of *Bacillus megaterium* B 205-3

(A) Morphology

The strain is a relatively large aerobic bacillus forming endospores and is positive to the Gram staining test. The spore has an oval or cylindrical shape. The GC content in DNA is 36 to 38%.

(B) Biological Properties (1) Egg Yolk Test: negative (2) Growth Conditions: The strain grows at a highest temperature of 35° to 45° C. and a lowest temperature of 3° to 20° C.

(C) Growth on Culture Media

The strain does not grow in an agar medium under an anaerobic condition.

The strain does not grow in a medium containing 0.001% of lysozyme.

Reference to the above-mentioned literature indicates that the strain is substantially in agreement with known *Bacillus megaterium*, and the strain was identified to be a strain of *Bacillus megaterium*.

The said microorganisms can be cultured by following a general culture method, for example, by inoculating the above-mentioned microorganism in a culture medium containing amino acid, casein decomposition product, glucose, phosphate, sulfate, etc., and culturing it at about 30°–37° C. with aeration and agitation.

A typical culture medium is illustrated below.

| (1) CI medium | in 10 liter |
|---|---|
| KH$_2$PO$_4$ | 60 g |
| K$_2$HPO$_4$ | 140 g |
| Na citrate . 2H$_2$O | 10 g |
| (NH$_4$)$_2$SO$_4$ | 20 g |
| Arginine | 2 g |
| Casamino acid | 2 g |
| Glucose | 50 g |
| MgSO$_4$ | 2 g |
| Tryptophan | 0.25 g |

(2) Bacto-Penassay broth (Difco)

The growth of the microorganism is measured by placing the culture broth in a cuvette and measuring transmittance thereof using light of a wavelength of 660 mμ.

After the culturing operation, cells are collected during a period ranging from the exponential phase to the initial stage of the stationary phase. The cells are subjected to ultrasonic oscillation and centrifugal separation as they are or after they are subjected to a lysozyme treatment to prepare a protoplast, whereby a cell-free extract is obtained. The so obtained cell-free extract is subjected to streptomycin sulfate treatment and ammonium sulfate fractionation, and then, gel filtration using Ultrogel ACA 44 or Sephadex G-100 and/or ion-exchange chromatography using DEAE-cellulose or phosphocellulose is conducted, whereby a novel DNA-decomposing enzyme of the endonuclease type is collected from the cells.

Namely, the enzyme of the present invention can be prepared by subjecting a cell-free extract obtained from cultured cells collected during a period ranging from the exponential phase to the initial stage of the stationary phase to a nucleic acid-removing treatment, an ammonium sulfate fractionating treatment, an ion-exchange chromatographical treatment or a gel filtration treatment or two or more of these treatments. The so obtained enzyme was proved to be a novel enzyme having the following physical and chemical properties.

The enzymes obtained in this manner have been proved to have the following physicochemical characteristics.

Physicochemical Characteristics of the Enzymes

(1) Activity and Substrate Specificity

As the substrate DNA of the enzymatic reaction there were prepared and used DNA's of Bacillus phage 105C (φ105 C.N) and Bacillus phage SPP 1 (SPP 1.N) propagated with *Bacillus amyloliquefaciens* IAM 1522, Bacillus phage φ105C (φ105C.168) and Bacillus phage SPP 1 (SPP 1.168) propagated with *Bacillus subtilis* ATCC 6051 and coli phage λ propagated with *Escherichia coli* B.

After the enzymatic reaction, when the size of the substrate DNA cleaved by the enzyme of the present invention and the number of the cleavage were examined by the electrophoretic patterns shown in the drawing.

The drawing is a photograph showing an agarose gel electrophoretic patterns of the substrate DNA treated by the enzyme of the present invention.

As shown in the drawing the molecule of DNA substrate DNA was segmented into fragments of specific size by the enzyme of the present invention.

The substrates used were as follows:

(1) DNA of untreated Bacillus phage φ105C.
(2) DNA of untreated E. coli phage λ.
(3) DNA of E. coli phage λ treated with Eco R I enzyme of *Escherichia coli* (control for comparison with (1) and (2)).

In the drawing, the symbols of the substrates have the following meanings.

(1) φ105C.168—Bacillus phage φ105C grown on *Bacillus subtilis* ATCC 6051
(2) SPP1.168—Bacillus phage SPP1 grown on *Bacillus subtilis* ATCC 6051
(3) φ104C.N—Bacillus phage φ105C grown on *Bacillus amyloliquefaciens* IAM
(4) SPP1.R—Bacillus phage SPP1 grown on *Bacillus subtilis* R
(5) λ—DNA of E. coli phage λ grown on *Escherichia coli* B
(6) λH—λDNA modified by *Bacillus amyloliquefaciens* H
(7) λDNA—untreated λDNA grown on *Escherichia coli* B
(8) 105C.168DNA—untreated φ105C.168DNA
(9) R.EcoRI—DNA of E. coli phage λ treated with EcoRI enzyme of *Escherichia coli*

The present inventors have named the novel enzymes "R. Bsu M," "R. Bsu 6633," "R. Bsu 1193," "R. Bsu 1231," "R. Bsu 1192," "R. Bsu 1145," "R. Bsu 1076," "R. Bsu 1114," "R. Bsu 1259," "R. Bce 14579," "R. Bce R," "R. Bce 170," "R. Bsu 1247," "R. Bce 1229," "R. Bme 205," "R. Bpu 1387," "R. Bme 899" and "R. Bsp 1286."

The enzyme names are based the general system of nomenclature described by H. O. Smith & D. Nathans: J. Mol. Biol., vol. 81, p. 419 (1973).

The names "Bsu," "Bam," "Bce," "Bme," "Bpu" and "Bsp" are derived as follows:

| Name | Genus | Species | Strain | Number |
|---|---|---|---|---|
| (1) Bsu M | Bacillus | subtilis | M | |
| (2) Bsu 6633 | " | " | | 6633 |
| (3) Bsu 1193 | " | " | | 1193 |
| (4) Bsu 1231 | " | " | | 1231 |
| (5) Bsu 1192 | " | " | | 1192 |
| (6) Bsu 1145 | " | " | | 1145 |
| (7) Bsu 1076 | " | " | | 1076 |
| (8) Bsu 1114 | " | " | | 1114 |
| (9) Bsu 1259 | " | " | | 1259 |
| (10) Bce 14579 | " | cereus | | 14579 |
| (11) Bce R | " | " | R | |
| (12) Bce 170 | " | " | | 170 |
| (13) Bsu 1247 | " | subtilis | | 1247 |
| (14) Bce 1229 | " | cereus | | 1229 |
| (15) Bme 205 | " | megaterium | | 205 |
| (16) Bpu 1387 | " | pumillus | | 1387 |
| (17) Bme 899 | " | megaterium | | 899 |
| (18) Bsp 1286 | " | sphaericus | | 1286 |

In the above, the abbreviations of the names of these enzymes are formed by combining the underlined head portions of the full names.

Further, the symbol "R." is an abbreviation for "Endonuclease R," and the symbol "R" is an abbreviation for "Restriction."

In addition, the term "EcoR 1" is derived as follows:

| Genus | Species | Strain | Number |
|---|---|---|---|
| Escherichia | coli | R | I |

Table 2

| | Microorganism Used | Name of Enzyme |
|---|---|---|
| (1) | *Bacillus subtilis* ATCC 6051 | BsuM |
| (2) | *Bacillus subtilis* ATCC 6633 | R. Bsu6633 |
| (3) | *Bacillus subtilis* IAM 1193 | R. Bsu1193 |
| (4) | *Bacillus subtilis* IAM 1231 | R. Bsu1231 |
| (5) | *Bacillus subtilis* IAM 1192 | R. Bsu1192 |
| (6) | *Bacillus subtilis* IAM 1145 | R. Bsu1145 |
| (7) | *Bacillus subtilis* IAM 1076 | R. Bsu1076 |
| (8) | *Bacillus subtilis* IAM 1114 | R. Bsu1114 |
| (9) | *Bacillus subtilis* IAM 1259 | R. Bsu1259 |
| (10) | *Bacillus cereus* ATCC 14579 | R. Bce14579 |
| (11) | *Bacillus cereus* Rf sm st ATCC 31293 | R. BceR |
| (12) | *Bacillus sp.* No. 170 ATCC 31292 | R. Bce170 |
| (13) | *Bacillus subtilis* IAM 1247 | R. Bsu1247 |
| (14) | *Bacillus cereus* IAM 1229 | R. Bce1229 |
| (15) | *Bacillus megaterium* B205-3 ATCC 31294 | R. Bme205 |
| (16) | *Bacillus pumillus* AHU 1387 | R. Bpu1387 |
| (17) | *Bacillus megaterium* IAM 1030 | R. Bme899 |
| (18) | *Bacillus sphaericus* IAM 1286 | R. Bsp1286 |

As is seen from the electrophoresis diagram of FIG. 1, the enzyme of *Bacillus subtilis* ATCC 6051 has a characteristic of decomposing DNA of bacillus phage φ 105C 168 and DNA of bacillus phage φ 105C N. The enzyme of *Bacillus subtilis* IAM 1076 and *Bacillus subtilis* IAM 1114 have the same substrate specificity, and it is seen that they have no activity to DNA of bacillus phage SPPI R.

The enzymes of *Bacillus subtilis* ATCC 6633, *Bacillus subtilis* IAM 1193, *Bacillus subtilis* IAM 1231 and *Bacillus subtilis* IAM 1192 cut each DNA into considerably small fragments, and they exhibit such specificity that they act even on DNA of SPPI phage modified with the strain R of *Bacillus subtilis*. It also is seen that the enzyme of *Bacillus subtilis* IAM 1247 has functions similar to those of the enzyme of Bacillus sp. No. 170 (ATCC 31292).

It is seen that the enzymes prepared from *Bacillus amyloliquefaciens* ATCC 23350, *Bacillus amyloliquefaciens* IAM 1523 and *Bacillus subtilis* IAM 1259 have such substrate specificity that they do not act on (i) λ phage DNA treated with the enzyme Bam NI, (ii) DNA of phage φ 105C 168 or (iii) λ phage DNA modified with the strain H of *Bacillus amyloliquefaciens*.

The enzyme of the present invention prepared from *Bacillus pumillus* AHU 1387 (Bpu 1387) was compared with the enzymes Bam NI, Bam NII and Bam NIII prepared from *Bacillus amyloliquefaciens* N (IAM 1522) according to the invention of the applicant's copending prior application (Japanese Patent Application No. 121671/75, Japanese Patent Disclosure 47980/1977) with respect to the substrate specificity on various DNS substrates to obtain results shown in Table 3.

As will be apparent from Table 3, the enzyme Bpul 387 is different from the enzymes Bam NI and Bam NII+Bam NIII with respect to functions on not only DNA's of bacillus phage φ 105, SPP1 and coli phage λ but also DNA of the plasmid (intracellular factor) λdv 1 of *Escherichia coli*, DNA of ColEl and DNA of simian virus 40.

Table 3

| | Number of Cut Portions | | |
|---|---|---|---|
| Substrate DNA | Bam NI | Bam NII + Bam NIII | Bpu1387 |
| bacillus phage φ 105C | 0 | ~9 + ~7 | 5 |
| bacillus phage φ 29 | 0 | 0 | not tested |
| bacillus phage M2 | 0 | 0 | not tested |
| bacillus phage SPP1 | 0 | 3 | 0 |
| coli phage λ | 5 | ~15 | 6 - 7 |
| λdv 1* | 1 | 2 or 3 | 1 |
| T7 | 0 | >14 | untested |
| ColE1* | 0 | 3 | 0 |
| SV 40** | 1 | >4 | 2 - 3 |

*dv 1, ColE1: plasmid (intracellular factor) of *Escherichia coli*
*SV 40: Simian virus 40

(2) Optimum pH

Each of the novel enzymes to the present invention has an optimum pH ranging from 7.2 to 8.3.

(3) Optimum Operation Temperature

Each of the novel enzymes of the present invention has an optimum operation temperature ranging from 35° C. to 37° C.

(4) Method for Measuring Potency

The activity of the enzyme is determined in the following manner. An enzyme sample is added to the reaction mixture containing 50 mM trishydrochloric acid buffer solution (pH=7.5), 5 mM MgCl$_2$, 0.2 mM EDTA, 5 mM β-mercaptoethanol and 0.1 mg of DNA for the enzymatic reaction. The mixture is treated at 37° C. for 50 minutes. Since formation of an acid-soluble nucleotide is not observed in the liquid after the reaction, the reaction product is subjected to electrophoresis using an agarose gel or neutral sucrose gradient centrifugal separation to examine the fragmentation of substrate DNA.

(5) Inhibition, Activation and Stabilization

Each of the enzymes of the present invention is activated by 1 millimole to 20 millimoles of Mg$^{2+}$ but a co-factor such as ATP or S-adenosyl methionine is unnecessary, and the activity is inhibited by more than 20 millimoles of Mg$^{2+}$ or more than 0.2 mole of NaCl. The enzyme (Bpul387) of *Bacillus pumillus* AHU 1387 is activated by 0.1 to 0.2 M of NaCl.

(6) Method of Purification

A method for purifying the present enzymes of R. Bam F and R. Bpu 1387 is shown in the following:

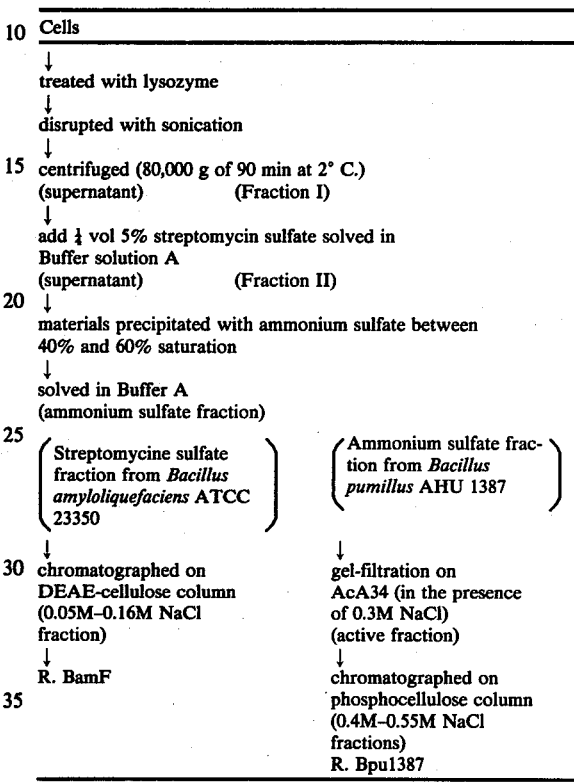

The enzymes of Bsu 1145 and Bce 14579 are obtained directly from the above-mentioned Fraction I. The enzymes of BsuM, Bsu 6633, Bsu 1193, Bsu 1231, Bsu 1192, Bsu 1076, Bsu 1114, Bam K, Bsu 1259, Bce R, Bce 170, Bsu 1247, Bce 1229, Bme 205, Bme 877 and Bsp 1286 are obtained directly from the above-mentioned Fraction II.

As will be apparent from the foregoing illustration, the enzymes of the present invention are novel nucleic acid-decomposing enzymes having such a high substrate specificity as to be capable specific nucleotide sequence on DNA and of cleaving such DNA at specific positions and forming DNA fragments having a specific size. According to the present invention, such novel enzymes can be advantageously prepared.

The process of the present invention will now be described in detail with reference to the following Examples.

EXAMPLE 1

*Bacillus pumillus* AHU 1387 was pre-cultured in 500 ml of a brain-heart infusion culture medium at 30° C. for 13 to 15 hours according to the shaking culture method. The pre-cultured medium was suspended in 10 liter of a CI culture medium having the following composition:

120 g of K$_2$HPO$_4$, 4 g of alginine hydrochloride, 280 g of KH$_2$PO$_4$, 100 g of glucose, 20 g of sodium citrate, 4 g of MgSO$_4$, 40 g of ammonium sulfate, 0.5 g of tryptophan and 4 g of Casamino acid (exclusive of vitamins).

The shaking culture was conducted at 37° C. for 6 hours to obtain cultured cells in the initial stage of the stationary phase. The so obtained culture liquid was subjected to centrifugal separation according to the continuous refrigerated centrifugal separation method to obtain about 13 g of cells. The cells were suspended in 20 ml of buffer solution A (containing 20 mM tris-Hcl buffer solution (pH=7.2), 0.1 mM EDTA, 2 mM $MgCl_2$ and 2 mM β-mercaptoethanol), and 13 m of egg-white lysozyme was added to the suspension. The resulting suspension was allowed to stand still at 37° C. for 35 minutes and subjected to sonication (20 Kc, 15 seconds, 4 times) and then to refrigerated centrifugal separation at 75,000 G for 60 minutes. Then, 10 ml of a 5% solution of streptomycin sulfate was added to the supernatant under agitation and the liquid was agitated for 20 minutes and subjected to refrigerated centrifugal separation. The supernatant was collected.

Ammonium sulfate was added to the supernatant under agitation over a period of 30 minutes so that a concentration of 35% saturation was attained. The mixture was agitated for 20 minutes. The resultant precipitate was removed by refrigerated centrifugal separation, and ammonium sulfate was added to the supernatant under agitation over a period of 30 minutes so that a concentration of 65% saturation was attained. The mixture was agitated for 30 minutes. The resultant precipitate was collected by freezing centrifugal separation and dissolved in the above-mentioned buffer solution A, and this fraction was dialyzed against the buffer solution overnight.

The dialyzed fraction was applied to the column of Ultrogel AcA 34 equilibrated with Buffer A supplemented with 0.3 M NaCl and 10% glycerol. The eluate from the column by the same buffer solution was dialyzed against Buffer A supplemented with 10% glycerol.

The dialyzed fraction was adsorbed on phosphocellulose (p 11; 1 cm×12 cm) equilibrated with the buffer solution A, followed by washing with the buffer solution A. Then, elution was conducted with the buffer solution A having a linear NaCl concentration gradient of 0 to 0.7 M, and it was found that the intended novel enzyme (Bpu 1387) was eluted between 0.4 and 0.55 M NaCl.

EXAMPLE 2

Instead of the microorganisms used in Examples 1 and 2, the microorganisms listed in Table 2 were cultured under the conditions described in Example 1.

Each of novel enzymes of Bsu 1145 and Bce 14579 was obtained from Fraction I.

Novel enzymes of Bsu M, Bsu 6633, Bsu 1193, Bsu 1231, Bsu 1192, Bsu 1076, Bsu 1114, Bam K, Bsu 1259, Bce R, Bce 170, Bsu 1247, Bce 1229, Bme 205, Bme 899 and Bsp 1286 were obtained from Fraction II.

What we claim is:

1. Endonuclease capable of selectively recognizing specific nucleic acids and cleaving the phospho-diester bond in the nucleic acids to produce nucleic acid fragments having discrete molecular weight, said enzyme being obtained from a cell-free extract of a species of genus Bacillus, which endonuclease is a member selected from the group consisting of:
(1) R. BsuM obtained from ATCC 6051
(2) R. Bsu6633 obtained from ATCC 6633
(3) R. Bsu1193 obtained from IAM 1193
(4) R. Bsu1231 obtained from IAM 1231
(5) R. Bsu1192 obtained from IAM 1192
(6) R. Bsu1145 obtained from IAM 1145
(7) R. Bsu1076 obtained from IAM 1076
(8) R. Bsu1114 obtained from IAM 1114
(9) R. Bsu1259 obtained from IAM 1259
(10) R. Bce14579 obtained from ATCC 14579
(11) R. BceR obtained from ATCC 31293
(12) R. Bce170 obtained from ATCC 31292
(13) R. Bsu1247 obtained from IAM 1247
(14) R. Bce1229 obtained from IAM 1229
(15) R. Bme205 obtained from ATCC 31294
(16) R. Bpu1387 obtained from AHU 1387
(17) R. Bme899 obtained from IAM 1030 and
(18) R. Bsp1286 obtained from IAM 1286.

2. Process for producing endonuclease defined in claim 1, which comprises cultivating a species of Genus Bacillus selected from the group consisting of ATCC 6051, ATCC 6633, IAM 1193, IAM 1231, IAM 1192, IAM 1145, IAM 1076, IAM 1114, IAM 1259, ATCC 14579, ATCC 31293, ATCC 31292, IAM 1247, IAM 1229, ATCC 31294, AHU 1387, IAM 1030 and IAM 1286 in a culture medium, collecting the cells thereof, obtaining cell free extract therefrom, fractionating the said extract and purifying the fractionated extract and obtaining
(1) R. BsuM obtained from ATCC 6051
(2) R. Bsu6633 obtained from ATCC 6633
(3) R. Bsu1193 obtained from IAM 1193
(4) R. Bsu1231 obtained from IAM 1231
(5) R. Bsu1192 obtained from IAM 1192
(6) R. Bsu1145 obtained from IAM 1145
(7) R. Bsu1076 obtained from IAM 1076
(8) R. Bsu1114 obtained from IAM 1114
(9) R. Bsu1259 obtained from IAM 1259
(10) R. Bce14579 obtained from ATCC 14579
(11) R. BceR obtained from ATCC 31293
(12) R. Bce170 obtained from ATCC 31292
(13) R. Bsu1247 obtained from IAM 1247
(14) R. Bce1229 obtained from IAM 1229
(15) R. Bme205 obtained from ATCC 31294
(16) R. Bpu1387 obtained from AHU 1387
(17) R. Bme899 obtained from IAM 1030 and
(18) R. Bsp1286 obtained from IAM 1286.

3. The endonuclease according to claim 1 which has optimum pH between 7.2 and 8.3.

4. The endonuclease according to claim 1 which has optimum operating temperature at 35°–37° C.

5. The endonuclease according to claim 1 which is activated by $Mg^{+2}$ in the amount of 1 millimole to 20 millimoles.

6. Endonuclease according to claim 1 wherein said enzyme is Endonuclease R Bsu M, which is capable of decomposing DNA of bacillus phage φ 105C 168 and DNA of bacillus phage φ 105CN.

7. Endonuclease according to claim 1 wherein said enzyme is Endonuclease R Bsu 6633 capable of acting on DNA of bacillus phage SPPI, modified with the strain R of *Bacillus subtilis*.

8. Endonuclease according to claim 1 wherein said enzyme is Endonuclease R Bsu 1193 capable of acting on DNA of bacillus phage SPPI, modified with the strain R of *Bacillus subtilis*.

9. Endonuclease according to claim 1 wherein said enzyme is Endonuclease R Bsu 1231 capable of acting on DNA of bacillus phage SPPI, modified with the strain R of *Bacillus subtilis*.

10. Endonuclease according to claim 1 wherein said enzyme is Endonuclease R Bsu 1192 capable of acting on DNA of bacillus phage SPPI, modified with the strain R of *Bacillus subtilis*.

11. Endonuclease according to claim 1 wherein said enzyme is Endonuclease R Bsu 1145.

12. Endonuclease according to claim 1 wherein said enzume is Endonuclease R Bsu 1076, which does not cleave DNA of bacillus phage SPPI R but cleaves bascillus phage 105C 168 and bacillus phage φ 105C N.

13. Endonuclease according to claim 1 wherein said enzyme is Endonuclease R Bsu 1114, which does not cleave DNA of bacillus phage SPPI R but cleaves DNA of bacillus phage φ 105C 168 and DNA of bacillus phage 100 105C N.

14. Endonuclease according to claim 1 wherein said enzyme is Endonuclease R Bsu 1259, which does not act on (1) λ phage DNA treated with the enzyme Bam NI (2) DNA of λ phage φ 105C 168 or (3) λ phage DNA modified with the strain H of *Bacillus amyloliquefaciens*.

15. Endonuclease according to claim 1 wherein said enzyme is Endonuclease R Bce 14579.

16. Endonuclease according to claim 1 wherein said enzyme is Endonuclease R Bce R.

17. Endonuclease according to claim 1 wherein said enzyme is Endonuclease R Bce 170.

18. Endonuclease according to claim 1 wherein said enzyme is Endonuclease R Bsu 1247.

19. Endonuclease according to claim 1 wherein said enzyme is Endonuclease R Bce 1229.

20. Endonuclease according to claim 1 wherein said enzyme is Endonuclease R Bme 205.

21. Endonuclease according to claim 1 wherein said enzyme is Endonuclease R Bpu 1387, which does not cleave bacillus phage SPPI and Col El but cleaves Bacillus phage φ 105C in 5 positions, cleaves Coli phage λ in 7 positions, λ dv 1 in 1 position, and SV40 in 2 positions, which endonuclease is activated by 0.1–0.2 M sodium chloride.

22. Endonuclease according to claim 1 wherein said enzyme is Endonuclease R Bme 899.

23. Endonuclease according to claim 1 wherein said enzyme is Endonuclease R Bsp 1286.

* * * * *